United States Patent
Kubbillum

[19]

[11] Patent Number: 6,018,989

[45] Date of Patent: Feb. 1, 2000

[54] METHOD AND APPARATUS FOR MEASURING THE PROPERTIES OF A FIBER OR COLLOID SUSPENSION

[75] Inventor: Peter Kubbillum, Diessen, Germany

[73] Assignee: Muetek Analytic GmbH, Germany

[21] Appl. No.: 08/919,671

[22] Filed: Aug. 28, 1997

[30] Foreign Application Priority Data

Aug. 30, 1996 [DE] Germany .......................... 196 35 318

[51] Int. Cl.[7] .................................................. G01N 11/06
[52] U.S. Cl. ........................................ 73/61.73; 73/53.04
[58] Field of Search .............................. 73/53.03, 53.04, 73/61.71, 61.72, 61.73, 61.78

[56] References Cited

U.S. PATENT DOCUMENTS

| | | | |
|---|---|---|---|
| 3,144,763 | 8/1964 | Mayo ...................................... | 73/53.04 |
| 3,330,151 | 7/1967 | Reinhall ................................. | 73/53.04 |
| 3,368,392 | 2/1968 | Miller ..................................... | 73/53.04 |
| 3,538,749 | 11/1970 | Danforth ............................... | 73/53.04 |
| 4,024,754 | 5/1977 | Alfthan .................................. | 73/53.04 |
| 4,389,879 | 6/1983 | Bach et al. ............................ | 73/53.03 |
| 4,554,051 | 11/1985 | Danforth ............................... | 73/53.03 |
| 5,408,185 | 4/1995 | Krah ...................................... | 324/453 |
| 5,495,751 | 3/1996 | Petzold et al. ........................ | 73/53.03 |
| 5,510,702 | 4/1996 | Erikson ................................. | 324/71.1 |

Primary Examiner—Michael Brock
Attorney, Agent, or Firm—St. Onge Steward Johnston & Reens LLC

[57] ABSTRACT

In the measurement of the properties of a fiber or colloid suspension for process control, e.g. in order to control a refiner, it is known that the fiber length is related to the rate at which water can be drained from a sample. In the present invention it is proposed to introduce the sample at a specified flow velocity into a lower section of an empty analyzer vessel that is subdivided by a filter into the lower section and an upper section situated above the filter. The sample is introduced in such a way that during the time it takes to fill the lower section of the analyzer vessel, sedimentation can occur in the sample fluid. Air is withdrawn from the upper section of the analyzer vessel at a specified rate of flow, by means of an exhaust or regulating valve. The rate at which the upper section is filled with filtrate can then be monitored as a measurement parameter. Alternatively or in addition, the filtrate can be sent to a measurement apparatus, in particular a polyelectrolyte measurement device.

14 Claims, 2 Drawing Sheets

METHOD AND APPARATUS FOR MEASURING THE PROPERTIES OF A FIBER OR COLLOID SUSPENSION

FIELD OF THE INVENTION

In many industrial processes the chemical and physical properties of fiber or colloid suspensions must be measured. In the production of paper and cardboard, such suspensions are primarily suspensions containing fibers, such as wood pulp, cellulose and the like wherein the fiber concentration is so high (7–8% fiber content) that the materials to be examined can be poured into a heap. In particular, it is of interest to measure the "freeness" of the fiber suspension, i.e. the rate at which water can be drained from it, which depends on the average fiber length (among other factors). Another parameter that can usefully be employed for process control is the polyelectrolyte concentration.

DESCRIPTION OF THE PRIOR ART

The polyelectrolyte concentration can be determined for example by measuring a flow potential in an apparatus such as is disclosed in the German patent DE 42 43 950 C1. A measurement of this kind must be carried out with a filtrate. For this and the measurement of the "freeness" of such suspensions filtration is necessary. However, filtering is highly problematic in this case, inasmuch as the filters become clogged very easily or rapidly and, in particular, thoroughly. Frequent cleaning of the filter is therefore unavoidable.

SUMMARY OF THE INVENTION

The object of the present invention is to provide a method and an apparatus for measuring the properties of a fiber or colloid suspensions which overcomes or substantially mitigates the aforementioned problems.

According to a first aspect of the present invention there is provided a method of measuring the properties of a fiber or colloid suspension for process control wherein solid and liquid components of a sample taken from a process are separated by filtering in an analyzer vessel having upper and lower sections separated by a filter, the method comprising steps of introducing a sample of the suspension into the lower section of the air-filled but otherwise empty analyzer vessel at a rate of flow which has been predetermined such that the time taken for lower section of the analyzer vessel to fill suffices to allow sedimentation of the sample;

withdrawing air from the upper section of the analyzer vessel at a specified rate of flow by way of a regulating valve; and at least one of (a) monitoring the rate at which the upper section of the analyzer vessel is filled with filtrate for use as a measurement parameter; and (b) withdrawing filtrate from the upper section of the analyzer vessel and forwarding same to a measurement apparatus.

It will be appreciated that in the invention the filtration rate, i.e. the speed with which the sample is transported to the analyzer vessel and passed through the filter, is adjusted in a suitable way. In this process, as a result of the fact that the air is withdrawn from the space above the filter only in a progressive manner, so that it is kept at a specified pressure, it is ensured that the differential pressure above the filter is maintained at specific, not excessively high values.

In turn, the speed with which the filtrate flows through the filter at the selected differential pressure can be taken as a measure of the freeness of the suspension. The shape of the curve relating filtration rate to differential pressure is also of particular interest here.

After a measurement has been made, the analyzer vessel must be emptied in order to be prepared for a new measurement. At the same time, the solid matter retained in the filter must be removed. For this purpose, as the vessel is being emptied, a negative pressure differential is preferably generated in its lower section, at least for certain periods. This negative pressure ensures that any fibers adhering to the surface of the filter become detached from it and the substantially fiber-free eluate or filtrate from the upper section of the analyzer vessel, or (in some cases, in addition to) fresh water or air, can clean the filter completely.

The negative pressure differential is preferably generated at the beginning of the emptying process, preferably in a stepwise or pulsed manner, which surprisingly has produced considerably better results than a continuous application of negative pressure.

According to a second aspect of the present invention there is provided apparatus for implementing the method of the first aspect wherein the properties of a fiber or colloid suspension for process control are measured, comprising an analyzer vessel defining a lower section and an upper section separated by a filter, the lower section of the vessel defining a sample inlet and the upper section of the vessel defining an air outlet;

first valve means disposed in the sample inlet to permit adjustment of the rate of flow at which a sample of the suspension flows into the analyzer vessel;

second valve means permitting regulation of the rate at which air can be withdrawn from the upper section of the vessel; and at least one of (a) means for measuring the rate at which the upper section of the analyzer vessel fills with filtrate; and (b) polyelectrolyte measurement means for determining polyelectrolyte content of the filtrate.

By virtue of the arrangement of the analyzer vessel of the apparatus with the sample inlet in the lower section beneath the filter and the upper section positioned above the filter, the action of gravity is employed to cause sedimentation of the suspension. In addition, as air can be removed from the analyzer vessel at the beginning of a measurement process at predetermined flow rates, the pressure in the upper section of the analyzer vessel can be maintained at particular values with the result that the differential pressure across the filter is not too great, which prevents clogging of the filter.

Preferably, an outlet valve is provided in the lower section of the analyzer vessel by way of which filtrate and filter cake can be removed from the analyzer vessel.

Advantageously, the outlet valve is mounted substantially vertically below the analyzer vessel and defines an outlet passageway therethrough which has a cross sectional area corresponding substantially to the cross sectional area defined by the lower section of the analyzer vessel. As a result, although the filter cake is a relatively firm solid, it can be removed with the assistance of the force of gravity and the diameter of the outlet valve is such that it cannot become plugged.

Preferably also, the outlet valve is constructed such that when it is opened, preferably abruptly, it generates a negative pressure differential in the lower section of the analyzer vessel. This pressure drop ensures that at the very beginning of the removal process the filter is cleared and can be cleaned by the liquid subsequently flowing through it.

Preferably also, the outlet valve comprises a tube-constricting valve. Such a tube-constricting valve generates the desired negative pressure when it is abruptly opened, because the interior volume of the valve in the opened state is greater than its volume in the closed state.

Preferably also, the upper section of the analyzer vessel defines a compressed-air inlet. This inlet enables pressure to be applied to the filtrate in order to empty the analyzer vessel. In addition, the upper section of the analyzer vessel preferably defines a rinsing water inlet which in a preferred embodiment supplies a rinsing nozzle by means of which the upper section of the analyzer vessel can be cleaned.

Advantageously, all the valves that come into contact with the sample fluid or components thereof are constructed as tube-constricting valves, which are particularly resistant to soiling.

BRIEF DESCRIPTION OF THE DRAWINGS

The various aspects of the present invention will now be described by way of example with reference to the accompanying drawings, wherein.

DESCRIPTION OF THE PREFERRED EMBODIMENTS

In the following description identical reference numbers are used for identical parts or parts with the same function.

Figure 1:
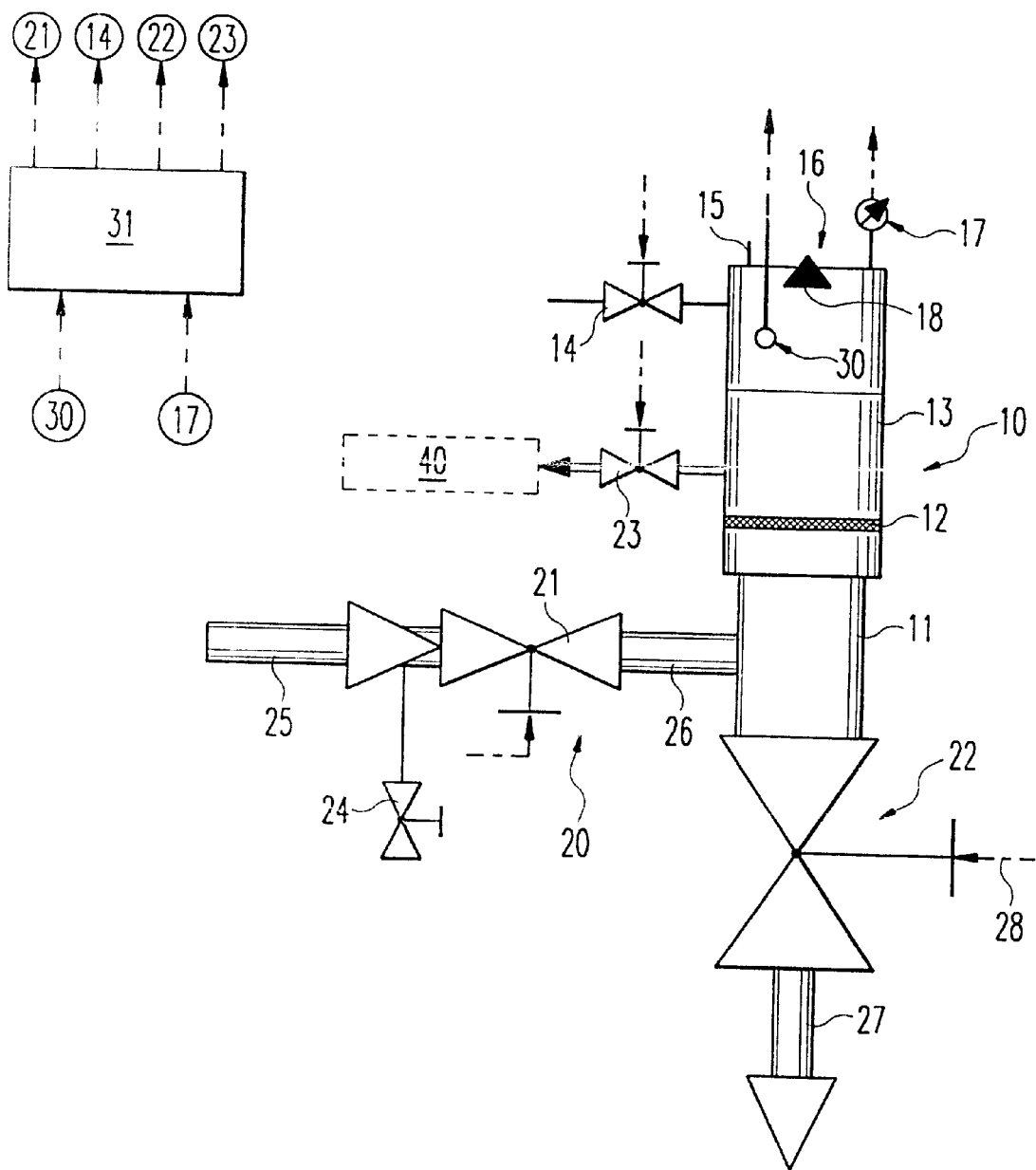
FIG. 1 is a schematic drawing of the layout of apparatus according to the invention.

FIG. 1 shows schematically an embodiment of the invention that comprises an analyzer vessel 10, which is basically composed of two sections arranged one vertically above the other, a lower section 11 and an upper section 13. The lower section 11 is separated from the upper section 13 by a substantially horizontal filter 12.

The arrangement is connected to a process conduit by way of a sampling line 25 that opens into a sample inlet 20 with a first valve 21. At the entrance to the first valve 21 or within the sampling line 25 a manual sampling valve 24 is provided, by way of which a sample can be taken from the overall apparatus for the purpose of examination.

At its exit side, the first valve 21 communicates with the lower section 11 of the analyzer vessel 10 by way of a connecting pipe 26.

Opening into the upper region of the upper section 13 is a regulating valve 14, by way of which gas (air) can flow out of the upper section 13 at a predetermined rate or against a predetermined back pressure. The maximal pressure prevailing in the upper section 13 can thus be adjusted by way of the valve 14.

There further opens into the upper section 13, although in a lower region thereof, a sample-extraction valve 23, by way of which liquid from the upper section 13 can be sent to sample-analyzing equipment such as a polyelectrolyte measurement device 40.

Also opening into the upper section 13 of the analyzer vessel 10 are a compressed-air pipe 15, which communicates with an adjustable source of compressed air, and a rinsing water pipe 16 that feeds a rinsing nozzle 18, so constructed that it can flush substantially the entire interior of the upper section 13 with rinsing water. In addition, a pressure meter 17 is provided to measure the pressure within the upper section 13.

Within the upper section 13 of the analyzer vessel 10 a sensor 30 is provided, the output signals from which are sent to a controlling and signal-evaluating unit 31. The said signals represent the level of the liquid within the upper section 13, so that the rate of filling can be determined by means of the unit 31. This controlling and signal-evaluating unit 31 also receives output signals from the pressure meter 17. In addition, the unit 31 controls the first valve 21, the regulating valve 14, the sample-extraction valve 23 and an outlet valve 22, which is disposed substantially vertically below the lower section 11 of the analyzer vessel 10 to allow a processed sample to be removed by way of an outlet pipe 27.

The operation of the apparatus in accordance with the method of the invention will now be described with reference to FIG. 1.

In an initial stage that precedes every sampling and testing procedure, the analyzer vessel 10 is substantially empty, i.e. filled with air. At this time the first valve 21 is opened by a certain amount, so that the fluid to be tested flows out of the sampling line 25, through the connecting pipe 26 and into the lower section 11 of the analyzer vessel 10. At the same time, the outlet valve 22 and the sample-extraction valve 23 are closed, whereas the regulating valve 14 is opened by a specified amount such that when the sample flows into the lower section 11, the (air) pressure in the analyzer vessel 10, in particular in its upper section 13, has a certain value as measured by the pressure meter 17. The valves 14 and 21 are adjusted in such a way that the level of the sample in the lower section 11 rises relatively slowly, so that during this sample-collection period some sedimentation can occur with the result that by the time the sample reaches the filter 12, its fiber content is already less than that of the fluid entering through the first valve 21. This influx is continued until the filtrate in the upper section 13 has reached a certain maximal level, which is detected by means of the sensor 30 and signalled to the controlling and signal-evaluating unit 31. The said unit simultaneously processes a signal representing the rate at which the level of liquid in the upper section 13 has risen during the procedure just described, so that with a specified pressure differential (determined by the valves 14 and 21) across the filter 12, a flow-velocity curve can be plotted and evaluated to find the "freeness" of the collected sample. The freeness in turn is a measure of the fibers contained in the sample, and in particular of their length.

After the desired liquid level in the upper section 13 has been reached, the sample-extraction valve 23 is opened. A certain portion of the sample can then be sent in the direction of the polyelectrolyte measuring device 40. After that, the emptying process can begin.

For emptying, while the first valve 21 is shut the valve 22 is opened; the latter, like the other valves that come into contact with the sample fluid, is constructed as a tube-constricting valve. As a result of the abrupt opening of the valve 22 a negative pressure is generated in the lower section 11, just below the filter 12, so that the fibers that had accumulated on the filter 12 during the filling process described above are essentially all cleared away from the filter 12.

As this emptying proceeds, the valves 14, 21 and 23 remaining closed, air is introduced through the compressed-air pipe 15, and after the upper section 13 has been completely emptied of filtrate, water is sent through the rinsing water pipe 16 and/or the rinsing nozzle 18 into the upper section 13 of the analyzer vessel 10, so that the vessel is not only emptied of filtrate but also cleaned. The cleaning liquid can be removed through valve 23 if it is opened, although of course it is not then sent to the polyelectrolyte measuring device 40.

Figure 2:
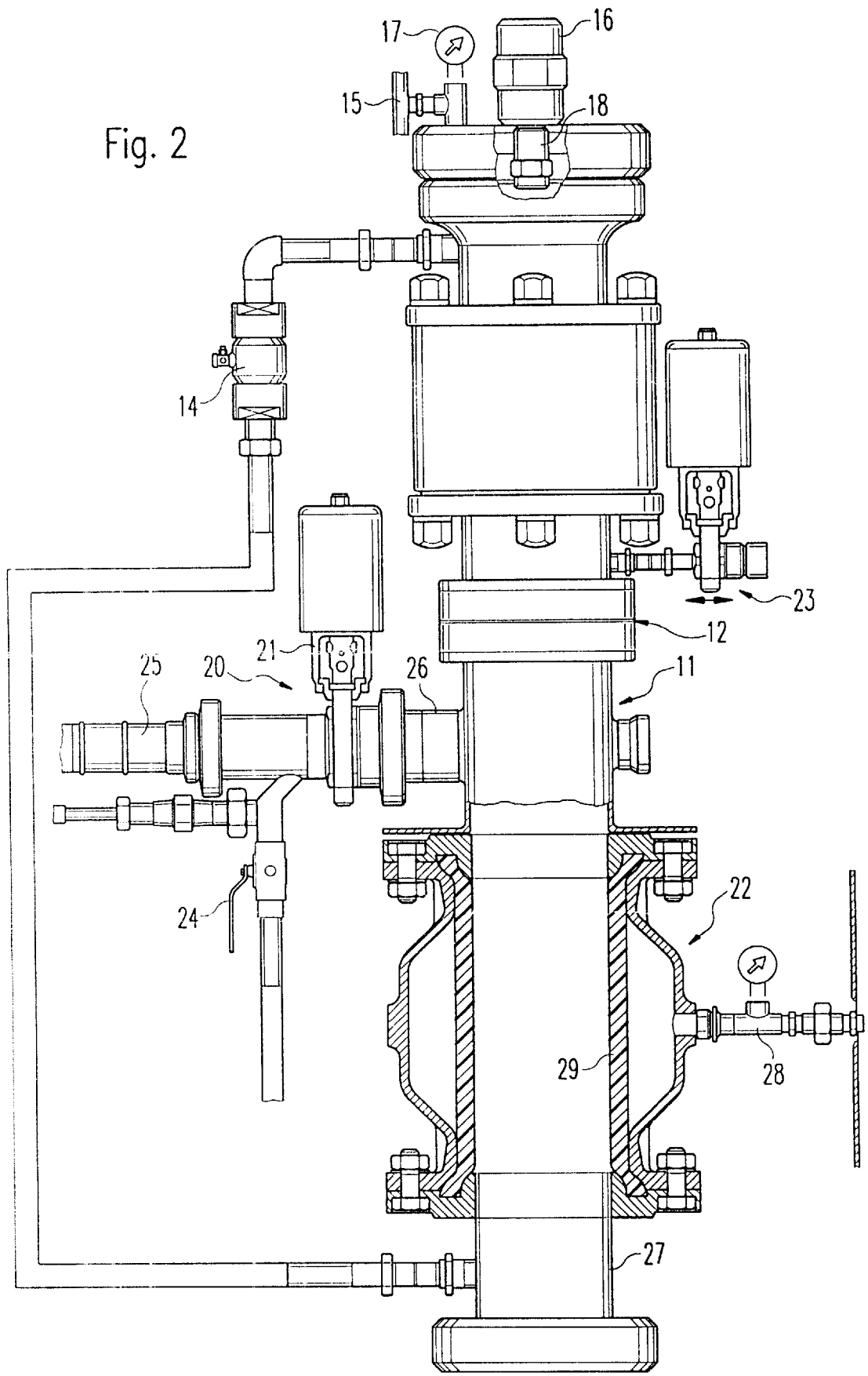
FIG. 2 is a partially cut-away elevation of one embodiment of the invention.

In the apparatus shown in somewhat greater detail in FIG. 2, parts identical to those in FIG. 1 are identified by the same numbers and are not discussed further here. However, FIG. 2 clarifies the construction of the tube-constricting valves preferably used in the present invention, as exemplified by the outlet valve 22. Here (as in the other tube-constricting valves) a control pipe 28 is provided that can apply pressure to the space between the housing of the valve 22 and an elastic tube 29, so that the tube 29 is compressed to such an extent as to close the passageway defined by the tube 29 through which fluid could otherwise flow. When the pressure is relieved by way of the control pipe 28, a suction effect comes into operation because the passageway of the tube 29 reopens, increasing the volume available in the valve 22. This is the suction effect mentioned at the outset, which "sucks away" material obstructing the filter 12.

What is claimed is:

1. A method for measuring the properties of a fiber or colloid suspension for process control wherein solid and liquid components of a sample taken from a process are separated by filtering in an analyzer vessel having upper and lower sections separated by a filter, the lower section having an outlet valve, the method comprising the steps of emptying the lower section of the analyzer vessel and filling the same by air;

introducing a sample of the suspension into the lower section of the air-filled analyzer vessel at a predetermined rate of flow;

withdrawing air from the upper section of the analyzer vessel at a specified rate of flow by way of a regulating valve;

monitoring the rate at which the upper section of the analyzer vessel is filled with filtrate for use as a measurement parameter; and producing a negative pressure differential in a stepwise or pulsed manner in the lower section of the analyzer vessel by opening the outlet valve in the lower section of the analyzer vessel, and emptying the analyzer vessel.

2. A method as claimed in claim 1, comprising the further step of filling the upper section of the analyzer vessel with compressed air during emptying the lower section of the analyzer vessel.

3. A method as claimed in claim 1, comprising the additional step of withdrawing filtrate from the upper section of the analyzer vessel and forwarding the same to a measurement apparatus.

4. Apparatus for measuring the properties of a fiber or colloid suspension for process control, comprising:

an analyzer vessel defining a lower section and an upper section separated by a filter, the lower section of the vessel defining a sample inlet and the upper section of the vessel defining an air outlet;

a first valve disposed in the sample inlet for sealing and emptying said lower section and for introducing a sample of suspension into the emptied lower section and for adjusting the rate of flow at which the sample of the suspension flows into the analyzer vessel;

a second valve for regulating the rate of air which can be withdrawn from the upper section of the vessel;

a device for measuring the rate at which the upper section of the analyzer vessel fills with a filtrate; and an outlet valve in the lower section of the analyzer vessel for removing a filtrate and a filter cake from the analyzer vessel by a stepwise negative pressure differential in the lower section wherein the outlet valve is constructed such that when it is opened it generates a negative pressure differential in the lower section of the analyzer vessel.

5. Apparatus as claimed in claim 4, wherein the outlet valve is mounted substantially vertically below the analyzer vessel and defines an outlet passageway therethrough which has a cross sectional area corresponding substantially to the cross sectional area defined by the lower section of the analyzer vessel.

6. Apparatus as claimed in claim 4, wherein the outlet valve comprises a tube-constricting valve.

7. Apparatus as claimed in claim 4, wherein the upper section of the analyzer vessel comprises a compressed-air inlet.

8. Apparatus for measuring the properties of a fiber or colloid suspension for process control, comprising:

an analyzer vessel defining a lower section and an upper section separated by a filter, the lower section of the vessel defining a sample inlet and the upper section of the vessel defining an air outlet;

a first valve disposed in the sample inlet for sealing and emptying said lower section and for introducing a sample of suspension into the emptied lower section and for adjusting the rate of flow at which the sample of the suspension flows into the analyzer vessel;

a second valve for regulating the rate of air which can be withdrawn from the upper section of the vessel;

a device for measuring the rate at which the upper section of the analyzer vessel fills with a filtrate; and an outlet valve in the lower section of the analyzer vessel for removing a filtrate and a filter cake from the analyzer vessel by a stepwise negative pressure differential produced in the lower section, wherein the outlet valve is constructed such that when it is opened it generates a negative pressure differential in the lower section of the analyzer vessel.

9. Apparatus as claimed in claim 8, wherein the upper section of the analyzer vessel comprises a rinsing water inlet.

10. Apparatus as claimed in claim 8, further comprising a rinsing nozzle operationally connected to the upper section of the analyzer vessel for cleaning the interior of the analyzer vessel.

11. Apparatus as claimed in claim 8, further comprising polyelectrolyte measurement device for determining the polyelectrolyte content of the filtrate.

12. Apparatus for measuring the properties of a fiber or colloid suspension for process control comprising:

an analyzer vessel defining a lower section and an upper section separated by a filter, the lower section of the vessel defining a sample inlet and the upper section of the vessel defining an air outlet;

a first valve disposed in the sample inlet to permit adjustment of the rate of flow at which a sample of the suspension flows into the analyzer vessel;

a second valve permitting regulation of the rate at which air can be withdrawn from the upper section of the vessel;

at least one of
  (a) device for measuring the rate at which the upper section of the analyzer vessel fills with filtrate, and
  (b) polyelectrolyte measuring device for determining the polyelectrolyte content of the filtrate; and an outlet valve in the lower section of the analyzer vessel by way of which filtrate and filter cake can be removed from the analyzer vessel, said outlet valve is constructed such that when it is opened it generates a negative pressure differential in the lower section of the analyzer vessel.

13. Apparatus for measuring the properties of a fiber or colloid suspension for process control comprising:

an analyzer vessel defining a lower section and an upper section separated by a filter, the lower section of the vessel defining a sample inlet and the upper section of the vessel defining an air outlet;

a first valve disposed in the sample inlet to permit adjustment of the rate of flow at which a sample of the suspension flows into the analyzer vessel;

a second valve permitting regulation of the rate at which air can be withdrawn from the upper section of the vessel;

at least one of
(a) device for measuring the rate at which the upper section of the analyzer vessel fills with filtrate, and
(b) polyelectrolyte measuring device for determining the polyelectrolyte content of the filtrate; and an outlet valve in the lower section of the analyzer vessel by way of which filtrate and filter cake can be removed from the analyzer vessel, said outlet valve comprises a tube-constricting valve.

14. Apparatus for measuring the properties of a fiber or colloid suspension for process control comprising:

an analyzer vessel defining a lower section and an upper section separated by a filter, the lower section of the vessel defining a sample inlet and the upper section of the vessel defining an air outlet;

a first valve disposed in the sample inlet to permit adjustment of the rate of flow at which a sample of the suspension flows into the analyzer vessel;

a second valve permitting regulation of the rate at which air can be withdrawn from the upper section of the vessel; and at least one of
(a) device for measuring the rate at which the upper section of the analyzer vessel fills with filtrate, and
(b) polyelectrolyte measuring device for determining the polyelectrolyte content of the filtrate;

said first valve comprises a tube-constricting valve.

* * * * *